United States Patent
Fisk et al.

(10) Patent No.: US 11,712,386 B2
(45) Date of Patent: Aug. 1, 2023

(54) PNEUMATIC SYSTEM BLOCKAGE DETECTION

(71) Applicant: Hill-Rom Services, Inc., Batesville, IN (US)

(72) Inventors: Brandon Fisk, Brookville, IN (US); Jnanesha Ramegowda, Batesville, IN (US); Gregory John Shannon, Indianapolis, IN (US); Frank Sauser, Cincinnati, OH (US); Michael Churilla, Harrison, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 230 days.

(21) Appl. No.: 16/926,958

(22) Filed: Jul. 13, 2020

(65) Prior Publication Data
US 2021/0015691 A1   Jan. 21, 2021

Related U.S. Application Data

(60) Provisional application No. 62/874,197, filed on Jul. 15, 2019.

(51) Int. Cl.
*A61G 7/057*   (2006.01)
*A47C 21/00*   (2006.01)
(Continued)

(52) U.S. Cl.
CPC ........ *A61G 7/05769* (2013.01); *A47C 21/003* (2013.01); *A47C 21/04* (2013.01);
(Continued)

(58) Field of Classification Search
CPC ............ A61G 7/05769; A61G 2203/34; A61G 7/05792; A61G 7/057; A61G 7/05784;
(Continued)

(56) References Cited

U.S. PATENT DOCUMENTS

| 5,379,471 A | 1/1995 | Holdredge |
| 7,225,488 B2 | 6/2007 | Wu |

(Continued)

FOREIGN PATENT DOCUMENTS

| CN | 102160837 A | 8/2011 |
| CN | 102499836 A | 6/2012 |

(Continued)

OTHER PUBLICATIONS

"Sensor." Oxford, Oxford—Lexico, www.lexico.com/en/definition/sensor.*

*Primary Examiner* — David R Hare
*Assistant Examiner* — Madison Emanski
(74) *Attorney, Agent, or Firm* — Price Heneveld LLP

(57) ABSTRACT

A patient support apparatus pneumatic system may include a mattress defining an interior and a pneumatic enclosure in fluid communication with the interior and comprising an inlet and an outlet. A blower may be in fluid communication with the interior and the pneumatic enclosure. A pressure sensor may be configured to detect a pressure at the outlet. A controller may be configured to monitor a speed of the blower and the pressure at the outlet for detecting at least one of an intake blockage condition and an exhaust blockage condition.

16 Claims, 6 Drawing Sheets

(51) Int. Cl.
  *A47C 21/04*    (2006.01)
  *A47C 27/08*    (2006.01)

(52) U.S. Cl.
  CPC ........ *A47C 27/083* (2013.01); *A61G 2203/12* (2013.01); *A61G 2203/34* (2013.01); *A61G 2203/70* (2013.01)

(58) Field of Classification Search
  CPC ............ A61G 2210/70; A61G 2203/30; A61G 2200/16; A47C 21/04; A47C 27/083; A47C 21/042; A61B 5/447; A61B 2562/0247
  See application file for complete search history.

(56) References Cited

U.S. PATENT DOCUMENTS

| | | | |
|---|---|---|---|
| 9,913,547 B2 * | 3/2018 | Driscoll, Jr. | ....... A61G 7/05769 |
| 2017/0049645 A1 | 2/2017 | Williams et al. | |
| 2017/0112697 A1 | 4/2017 | Tanaka | |
| 2017/0354768 A1 * | 12/2017 | Bushko | ................. A61M 1/743 |
| 2017/0363096 A1 * | 12/2017 | Fleming | ............ A61M 16/0069 |

FOREIGN PATENT DOCUMENTS

| | | | |
|---|---|---|---|
| CN | 105982800 A | 10/2016 | |
| EP | 3132780 A1 * | 2/2017 | ............... A61G 7/02 |
| JP | H06154483 A * | 11/1992 | ............ D06F 58/00 |
| JP | H06182096 A * | 12/1992 | ............ D06F 58/00 |
| JP | H06154483 A | 6/1994 | |

* cited by examiner

PNEUMATIC SYSTEM BLOCKAGE DETECTION

CROSS-REFERENCE TO RELATED APPLICATIONS

This application claims priority to U.S. Provisional Application No. 62/874,197, filed on Jul. 15, 2019, entitled, "PNEUMATIC SYSTEM BLOCKAGE DETECTION," the disclosure to which is hereby incorporated herein by reference in its entirety.

FIELD OF THE DISCLOSURE

The present disclosure generally relates to pneumatic system blockage detection, and more specifically to a pneumatic system intake and exhaust blockage detection for a patient support apparatus.

SUMMARY OF THE DISCLOSURE

According to one aspect of the present disclosure, a patient support apparatus pneumatic system includes a mattress that defines an interior. A pneumatic enclosure is in fluid communication with the interior. The pneumatic enclosure includes an inlet and an outlet. A blower is in fluid communication with the interior and the pneumatic enclosure. A pressure sensor is configured to detect a pressure at the outlet. A controller is configured to monitor a speed of the blower and the pressure at the outlet for detecting at least one of an intake blockage condition and an exhaust blockage condition.

According to another aspect of the present disclosure, a pneumatic system for a patient apparatus includes a pneumatic enclosure having an inlet and an outlet. A blower is in fluid communication with the inlet via a first flexible conduit. A microclimate management layer is in fluid communication with the outlet via a second flexible conduit. A pressure sensor is configured to detect pressure within the pneumatic enclosure. A controller adjusts a speed of the blower to maintain a predetermined pressure within the pneumatic enclosure. The controller is configured to detect at least one of an intake blockage condition and an exhaust blockage condition when the speed of the blower is outside a predetermined speed range.

According to another aspect of the present disclosure, a method of operating a mattress pneumatic system includes detecting pressure within a pneumatic enclosure. A detected pressure is compared with a predetermined pressure value. A speed of a blower is adjusted in response to a pressure differential between the detected pressure and the predetermined pressure value. The speed of the blower is compared to a predetermined speed range. A user is alerted of at least one of an intake blockage condition and an exhaust blockage condition when the speed of the blower is outside the predetermined speed range.

These and other features, advantages, and objects of the present invention will be further understood and appreciated by those skilled in the art by reference to the following specification, claims, and appended drawings.

DETAILED DESCRIPTION

Figure 1:
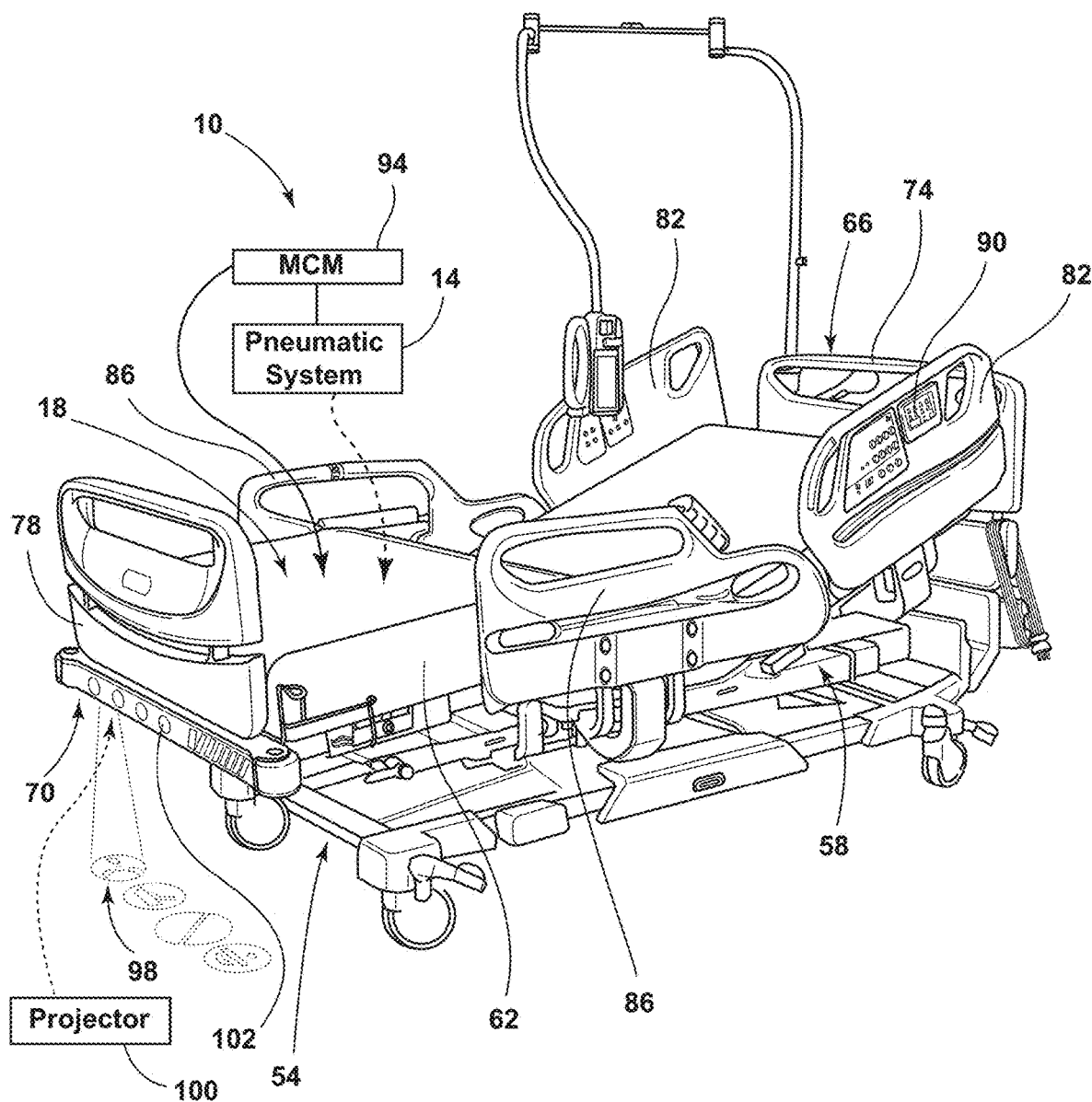
FIG. 1 is a top perspective view of a patient support apparatus according to various aspects described herein.

The present illustrated embodiments reside primarily in combinations of method steps and apparatus components related to a patient support apparatus pneumatic system. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-6, reference numeral 10 generally designates a patient support apparatus in the form of a bed. A patient support apparatus pneumatic system 14 includes a mattress 18 that defines an interior 22. A pneumatic enclosure 26 is in fluid communication with the interior 22 and includes an inlet 30 and an outlet 34. A blower 38 is in fluid communication with the interior 22 and the pneumatic enclosure 26. A pressure sensor 42 is configured to detect a pressure at the outlet 34. A controller 46 is configured to monitor a speed of the blower 38 and the pressure at the outlet 34 for detecting at least one of an intake blockage condition 48 and an exhaust blockage condition 50.

Referring now to FIG. 1, the patient support apparatus 10 may include a hospital bed. While described as the patient support apparatus 10, it is within the scope of the disclosure that the patient support apparatus 10 may include a bed frame, a mattress, or any suitable structure for supporting a patient, including, but not limited to: other types of beds, surgical tables, examination tables, stretchers, and the like.

The patient support apparatus 10 may include a frame, which may be in the form of a base frame 54. An upper frame 58 may be coupled with the base frame 54. The upper frame 58 may be operable between raised, lowered, and tilted positions relative to the base frame 54. The mattress 18 of the patient support apparatus 10 defines a patient support surface and is supported by one of the base frame 54 and the upper frame 58. The mattress 18 may be in the form of a cushion including a foam base and multiple layers. In some examples, bladders, springs, beads, gel, and the like may be included in the mattress 18. In examples where the mattress 18 includes bladders or cells, the pneumatic system 14 may control airflow in and out of various air bladders or cells of the mattress 18. The bladders or cells may be adjusted between inflated and deflated conditions to provide comfort or treatment to a patient on the mattress 18. Furthermore, the mattress 18 may be encased in a mattress cover 62, which is generally removable from the mattress 18 for washing or replacing.

In the illustrated configuration of FIG. 1, the patient support apparatus 10 includes a head end 66 and a foot end 70. A headboard 74 is provided at the head end 66 and a footboard 78 is provided at the foot end 70. The patient support apparatus 10 also includes a pair of head siderail assemblies 82 and a pair of foot siderail assemblies 86. In some examples, an interface 90, which may be a graphical user interface (GUI), is coupled with an external side of at least one siderail of the head and foot siderail assemblies 82, 86. While FIG. 1 illustrates the interface 90 coupled to the external side of one of the head siderail assembly 82, it is also contemplated that the interface 90 may be coupled to any suitable component of the patient support apparatus 10 for access by a user or caregiver. For example, the interface 90 may be coupled to one of the foot siderail assemblies 86, the footboard 78, or the headboard 74.

The patient support apparatus 10 may include various mattress function technologies, such as a microclimate management (MCM) system 94 disposed in the mattress 18. The MCM system 94 may address shear, friction, pressure, and moisture properties of the mattress 18 in order to optimize patient comfort and to keep a patient's skin cool and dry, which may aid in prevention of complications during patient recovery including preventing wounds, bed sores, etc. The MCM system 94 may automatically make adjustments based on predetermined therapy functions or may manually make adjustments based on the user input commands received from the interface 90 by a caregiver. The pneumatic system 14 of the patient support apparatus 10 is in fluid communication with the MCM system 94.

In some examples, an MCM system status floor indicator 98 may be projected as an image onto the floor surface from a projector 100 coupled with the foot end 70 of the patient support apparatus 10. The image generally indicates information regarding the MCM system 94, which may include whether the MCM system 94 is active or inactive. Alternatively, indicators 102 may be provided at the foot end 70 for displaying information regarding the MCM system 94.

Figure 2:
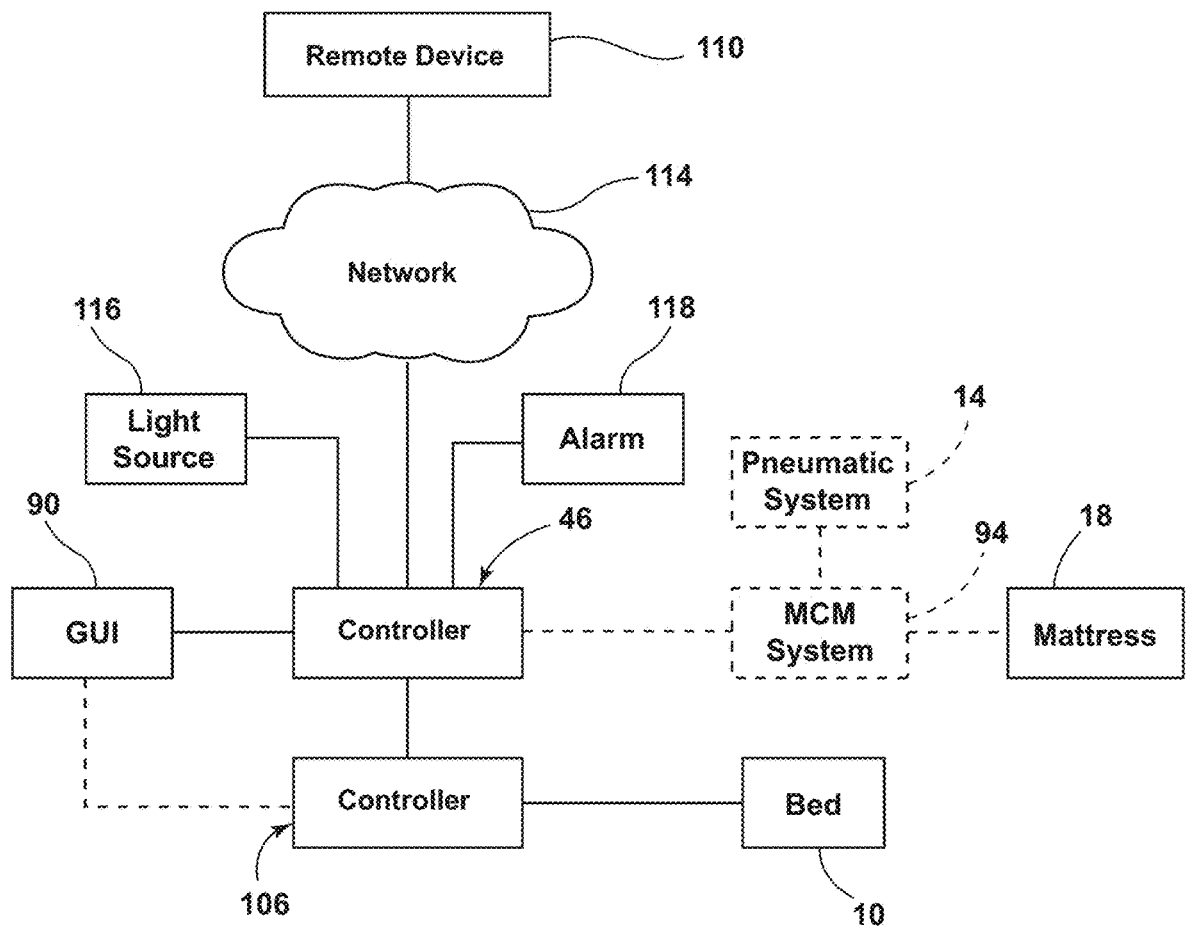
FIG. 2 is a block diagram of a controller for the patient support apparatus of FIG. 1 according to various aspects described herein.

With reference now to FIG. 2, the controller 46 may be in electrical communication with the patient support apparatus 10 and/or the mattress 18 for gathering input, processing the input, and generating an output in response to the input. In some examples, the controller 46 is in the form of a first controller configured to control the mattress 18 and a second controller 106 may control the patient support apparatus 10. However, it is within the scope of the disclosure for a single controller 46 to control both the patient support apparatus 10 and the mattress 18. In some examples, the controller 46 may be in the form of a microcontroller and may include one or more central processing units (CPUs), or microprocessors, memory, and programmable input/output ports. The controller 46 may execute programs to automatically control functions and algorithms for the mattress 18, including the pneumatic system 14 and the MCM system 94. The input may be provided to the controller 46 from various sensors in electrical communication with the mattress 18, or from user input. The user input, including input to the interface 90, may be provided by the caregiver or the patient in order to command the operation of functions of the mattress 18.

In some examples, the controller 46 is in communication with a remote device 110 via a network 114, such as the internet, a hospital wireless infrastructure, such as an electronic medical record (EMR), an Ethernet, and the like. The network 114 may have one or more various wired or wireless communication mechanisms, including any combination of wired (e.g., cable and fiber) or wireless communications and any network topology or topologies. Exemplary communication networks include wireless communication networks, such as, for example, a Bluetooth® transceiver, a ZigBee® transceiver, a Wi-Fi transceiver, an IrDA transceiver, an RFID transceiver, etc.

The controller 46 and the remote device 110 may include circuitry configured for bidirectional wireless communication. Additional exemplary communication networks include local area networks (LAN) and/or wide area networks (WAN), including the Internet and other data communication services. It is contemplated that the controller 46 and the remote device 110 may communicate by any suitable technology for exchanging data. In this way, the mattress 18 may be fully integrated with the patient support apparatus 10. For example, the controller 46 may transmit a status of the mattress 18 and/or health to the patient support apparatus 10 and to the hospital wireless infrastructure, which may be useful for the hospital or for maintenance of the patient support apparatus 10. Furthermore, mattress therapy or functions of the mattress 18 may be configured remotely by the remote device 110. The remote device 110 may be a remote handheld unit, such as, for example, a phone, a tablet, a portable computer, a wearable device, etc., or may be a device associated with a hospital or another medical facility.

The pneumatic system 14 may be associated with a light source 116 and an alarm 118 for communicating information regarding the pneumatic system 14 to the user, as will be discussed in greater detail below. The light source 116 and the alarm 118 may be included in, or otherwise operably coupled with, at least one of the bed 10, the mattress 18, the interface 90, and the remote device 110 for outputting the alarm signal. The alarm 118 may have any configuration for outputting the selected alarm signal (e.g., a speaker, a light source, a display, etc.). Moreover, the light source 114 may be any practicable type or number of light sources without departing from the teachings herein.

Figure 3:
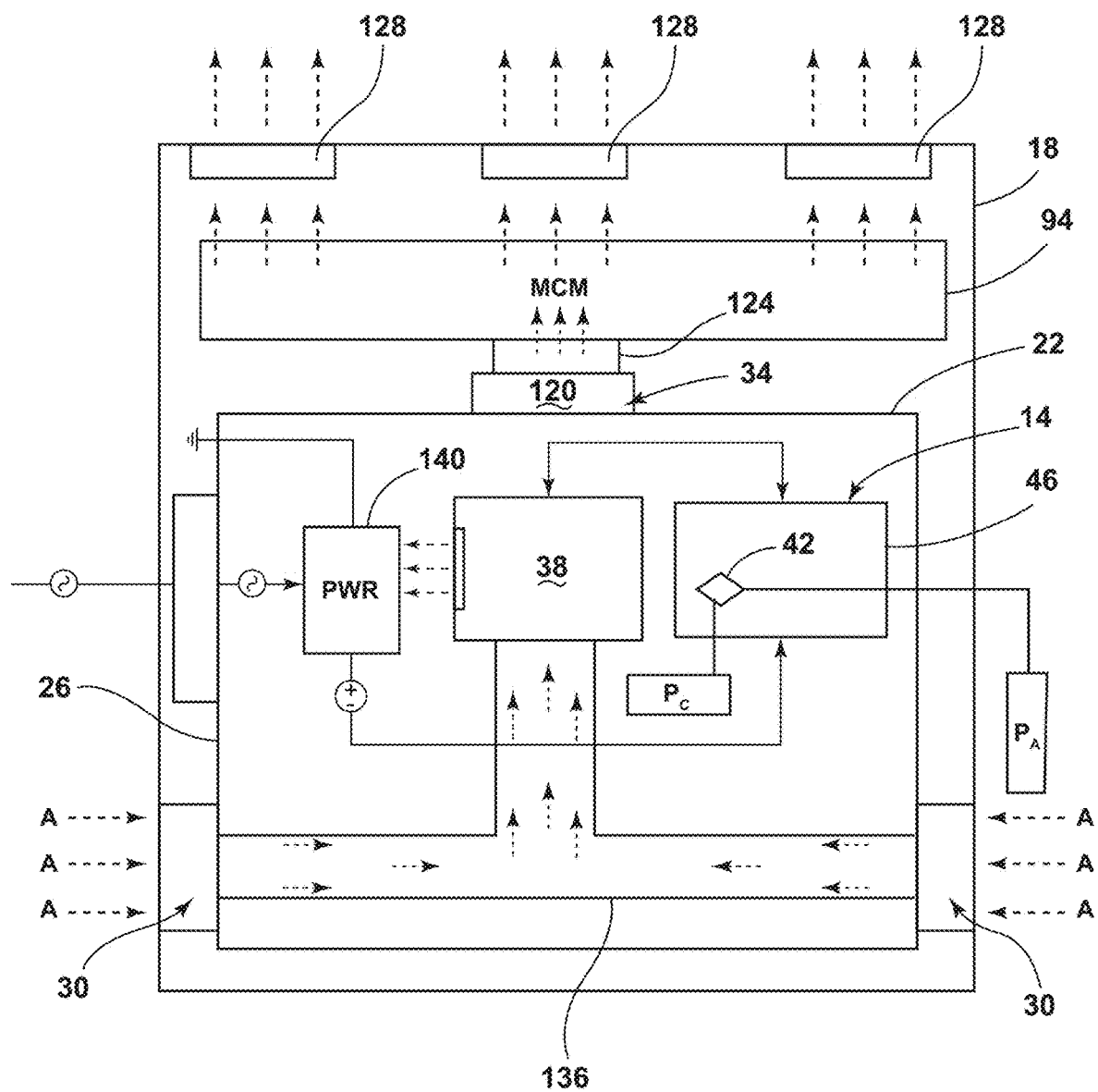
FIG. 3 is a schematic view of a patient support apparatus pneumatic system according to various aspects described herein.

Referring now to FIG. 3, a schematic view of an example of the pneumatic system 14 of the patient support apparatus 10 is illustrated. The interior 22 of the mattress 18 is in fluid communication with the MCM system 94, which may be in the form of an MCM layer, and the pneumatic enclosure 26 or chamber. It is within the scope of the disclosure for the MCM system 94 and the pneumatic enclosure 26 to be located in any suitable position for being in fluid communication with the interior 22, which may include being located at least partially within the interior 22.

It is generally contemplated that the pneumatic enclosure 26 will be in fluid communication with the MCM system 94 via the outlet 34, which may include an interface connector 120. The interface connector 120 may be any suitable connecting component or combination of components including various types of valves, vents, conduits, ports, hoses, etc. for controlling the flow of fluid between the pneumatic enclosure 26 and the MCM system 94. For example, as illustrated in FIG. 3, the interface connector 120 and the MCM system 94 are connected via a flexible conduit 124. While illustrated as a single outlet 34 in FIG. 3, the pneumatic system 14 may include multiple outlets 34 and/or interface connectors 120. Additionally, the MCM system 94 may include a plurality of vents 128 configured to provide air flow for various mattress therapies.

Furthermore, the pneumatic enclosure 26 may include at least one intake or inlet 30 in fluid communication with ambient air, A. The inlets 30 may be any suitable connecting component or combination of components including various types of valves, vents, conduits, ports, hoses, etc. for controlling the flow of fluid between the ambient atmosphere and the pneumatic enclosure 26. The inlets 30 of the pneumatic enclosure 26 may be in fluid communication with an air source, such as a pump or blower 38, for pressurizing the pneumatic enclosure 26. In some examples, the inlets 30 are fluidly coupled to the blower 38 via one or more flexible conduits 136. The blower 38 may be in electrical communication with the controller 46. Thus, the controller 46 can monitor the speed of the blower 38. Moreover, the speed of the blower 38 may be measured in revolutions per minute (RPM). In examples where a rotary vane pump is employed as the air source, the controller 46 may monitor the speed of the vanes.

As illustrated in FIG. 3, the controller 46 is in communication with the pneumatic system 14 and at least one pressure sensor 42. For example, the pressure sensor 42 may be in the form of a differential pressure transducer, however the pressure sensor 42 may be any suitable sensor configured to provide a signal to the controller 46 indicative of a pressure, such as a vacuum pressure sensor, a gauge pressure sensor, a sealed pressure sensor, and the like. In some examples, the pressure sensor 42 may be configured to measure a chamber pressure, $P_C$ and/or an ambient pressure, $P_A$. The difference between ambient pressure, $P_A$ and chamber pressure, Pc provides the actual gauge pressure inside of the pneumatic enclosure 26 relative to atmospheric pressure. The pressure sensor 42 may be configured to measure a pressure at a variety of locations, which may include at the inlet(s) 30 and the outlet(s) 34. Furthermore, the controller 46 may be in electrical communication with a power supply 140 that provides power to the blower 38.

Figure 5:
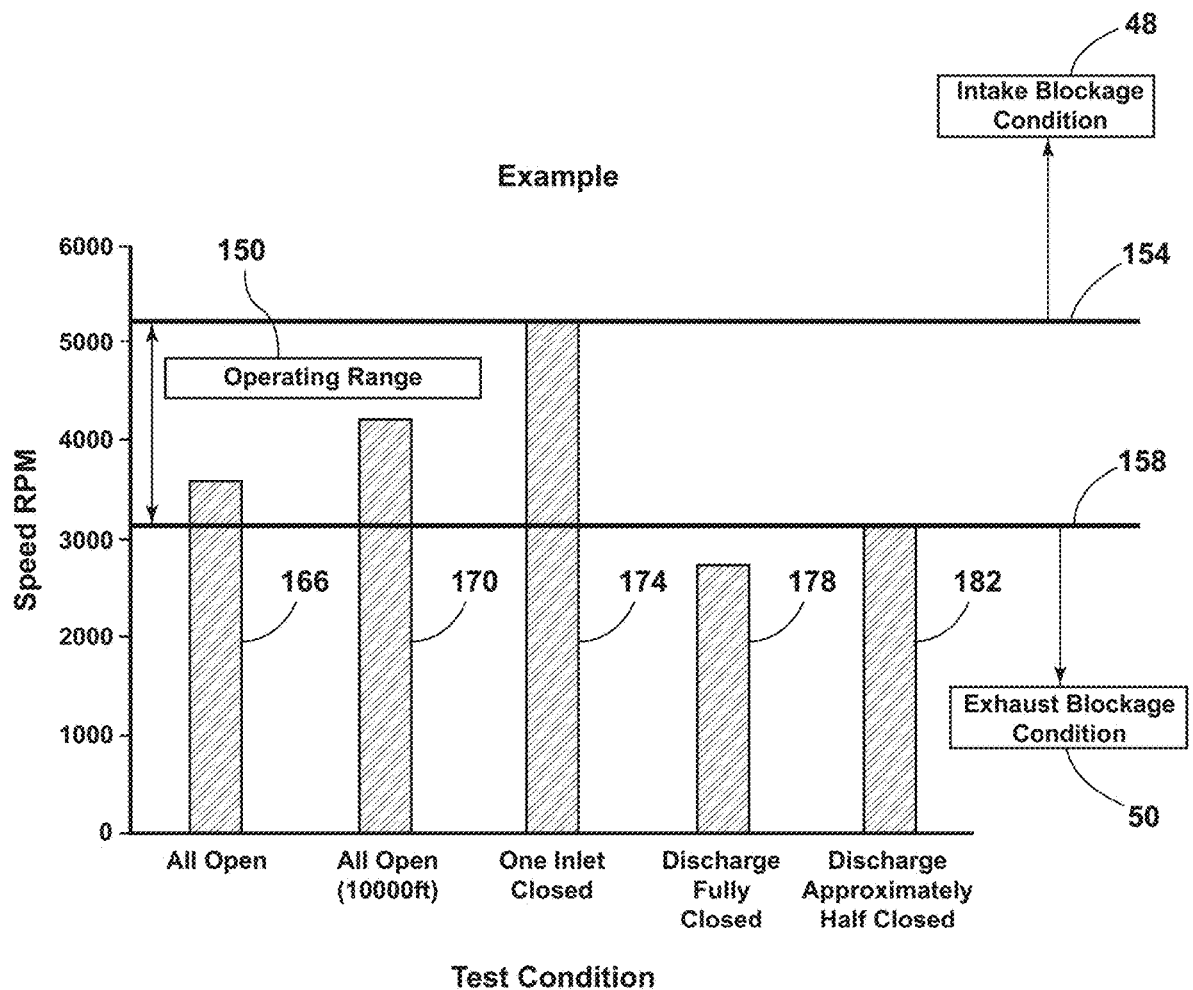
FIG. 5 is a graph illustrating an operating range according to various aspects described herein.

The controller 46 may monitor the chamber pressure, Pc, which may be compared to a predetermined pressure value for maintaining optimal performance of the MCM system 94. The chamber pressure, Pc may be indicative of the discharge pressure, or pressure at the outlet 34. It is generally contemplated that the controller 46 may command the blower 38 to increase or decrease speed in order to maintain the predetermined pressure value. The predetermined pressure value may be a range of pressure values indicative of an operating range, or ideal conditions where the pneumatic system 14 is working within a range of acceptable variability. In some examples, the predetermined pressure value(s) may vary depending on a true altitude value, or height above mean sea level, of the patient support apparatus 10. In further examples, the predetermined pressure value may be a default value, or a value input provided by a user or caregiver. The predetermined pressure value, or range, may correspond to a predetermined speed range 150 for the blower 38, which is illustrated in FIG. 5. In this way, the blower 38 may operate within the predetermined speed range 150 to maintain the predetermined pressure range. Under a fault condition, the blower 38 may be operating outside of the predetermined speed range 150.

Figure 4:
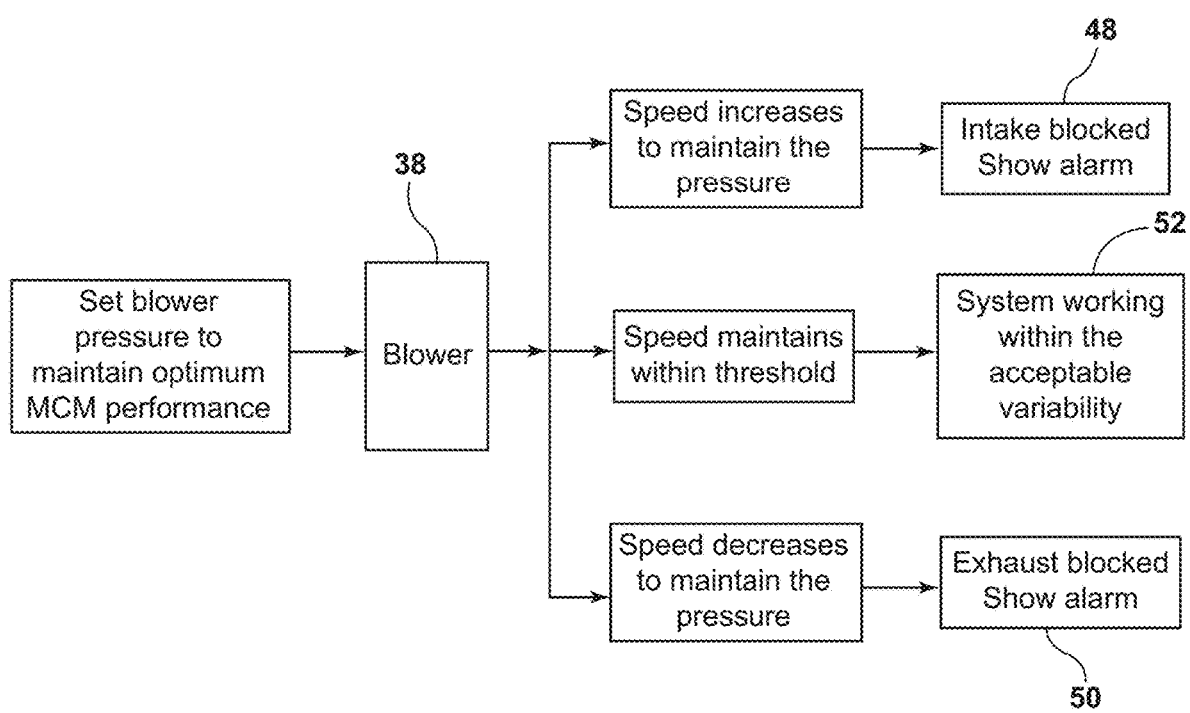
FIG. 4 is a flow chart illustrating an intake blockage condition and an exhaust blockage condition according to various aspects described herein.

Referring to FIG. 4, an intake blockage condition 48, an exhaust blockage condition 50, or both conditions may constitute a fault condition. A pressure drop at the inlet 30 may indicate that the intake blockage condition 48 has occurred. The intake blockage condition 48 may result from a variety of situations. Examples of an intake blockage condition 48 include a kink in the flexible conduit 136 or an item, such as a sheet, improperly situated at the inlet 30. During an intake blockage condition 48, the controller 46 may increase the speed of the blower 38 to compensate for the loss of pressure in order to maintain the predetermined pressure value. As will be described in further detail herein, the patient support apparatus pneumatic system 14 is configured to alert a caregiver when an intake blockage condition 48 exists.

Referring once again to FIG. 4, a pressure increase at the outlet 34 may indicate that the exhaust blockage condition 50 has occurred. The exhaust blockage condition 50 may result from a variety of situations. Examples of an exhaust blockage condition 50 include a kink in the conduit 124 or a disconnection of the interface connector 120 from the MCM system 94. During an exhaust blockage condition 50, the controller 46 may decrease the speed of the blower 38, as air compression requires less volume of air in order to maintain the predetermined pressure value. As with the intake blockage condition 48, the patient support apparatus pneumatic system 14 is also configured to alert a caregiver when an exhaust blockage condition 50 exists.

Referring to FIGS. 4 and 5, when the blower 38 is maintaining speed and the chamber pressure, Pc is maintained at the predetermined pressure value or within a predetermined pressure range, an optimal condition 52 may be detected. The speed of the blower 38 in the optimal condition 52 falls between the speed of the blower 38 in the intake blockage condition 48 and the exhaust blockage condition 50. The optimal condition 52 generally indicates that the pneumatic system 14 is operating optimally and within the acceptable range of variability. Additionally, when the optimal condition 52 is detected, the blower 38 is operating within an operating speed range 150 and the speed of the blower 38 is maintained in the operating speed range 150.

Referring to FIG. 5, an example of the speed range, or the operating speed range 150, is graphically illustrated. The intake blockage condition 48, the exhaust blockage condition 50, and the operating speed range condition 150 are illustrated as exemplary conditions, which may vary depending on a variety of factors, such as the type of air source or blower 38 used. In some examples, the intake blockage condition 48 is determined, or detected, when the speed of the blower 38 is at or above a predetermined upper threshold value 154. Similarly, the exhaust blockage condition 50 may be detected when the speed of the blower 38 is at or below a predetermined lower threshold value 158. Thus, the operating speed range condition 150 may include blower 38 speeds between the predetermined upper threshold value 154 and the predetermined lower threshold value 158.

In exemplary blower applications, a patient support apparatus pneumatic system 166 having all open inlets 30 and outlets 34 may operate at blower 38 speeds of approximately 3,400 RPM. In applications where a patient support apparatus pneumatic system 170 has all open inlets 30 and outlets 34 and is operating at a higher altitude, such as 10,000 feet (3,048 meters), a normal operation blower 38 speed may be approximately 4,200 RPM. In conditions above sea level where a patient support apparatus pneumatic system 174 includes at least one inlet 30 closed, or blocked, the blower 38 may run at speeds of approximately 5,100 RPM or greater. In conditions where a patient support apparatus pneumatic system 178 includes a discharge or the outlet 34 is fully closed, or blocked, the blower 38 may run at speeds of approximately 2,700 RPM or less. Similarly, in conditions where a patient support apparatus pneumatic system 182 includes a discharge or the outlet 34 is partially, or approximately half closed, or blocked, the blower 38 may run at speeds of approximately 3,100 RPM or less. As such, the predetermined upper threshold value 154 may be approximately 5,000 RPM and the predetermined lower threshold value 158 may be approximately 3,100 RPM.

Upon detection of either of the intake blockage condition 48 or the exhaust blockage condition 50 when monitoring the blower 38 speed and pressure feedback from the pressure sensor 42, the controller 46 may output an alarm signal. The alarm signal may include a blockage status indicator on a display, such as the status floor indicator 98, as one of the indicators 102, on the interface 90 (FIG. 1), etc. Alternatively, the alarm signal may be any suitable alert, or notification, for indicating at least one of the intake blockage condition 48 and the exhaust blockage condition 50, which may include, but is not limited to: an audible alarm on a local or remote device 110, a notification pushed to a display including the interface 90 or a display on the remote device 110, an interface lockout mode where the interface 90 may not be accessible until a blockage status notification is acknowledged and a light source 116 configured to selectively illuminate.

The controller 46 may be configured to monitor the frequency of detected intake blockage conditions 48 and exhaust blockage conditions 50, which may be stored as a count in a memory of the controller 46 or the remote device 110. The count of detected intake blockage conditions 48 may be separate from, or in addition to, the count of detected exhaust blockage conditions 50. A predetermined frequency threshold value may be a certain number of detected intake blockage conditions 48 and/or exhaust blockage conditions 50 where an action may be initiated when the predetermined frequency threshold value is reached or surpassed.

In some examples, upon reaching the predetermined frequency threshold value, the action may include disabling the blower 38. The action may further include the alarm signals as previously discussed, such as the blockage status indicators and/or notifications. In specific examples, upon reaching a first predetermined frequency threshold value, the controller 46 may selectively illuminate a light source 116 at a first rate. The light source 116 may be in the form of an indicator located on any suitable location of the patient support apparatus 10 and/or the remote device 110, such as the indicator 102. Additionally, upon reaching a second predetermined frequency threshold value, the controller 46 may selectively illuminate the light source 116 at a second rate, which is different from the first rate. In some examples, the second rate is higher than the first rate. In additional or alternative examples, the second rate may include selectively illuminating the light source 116 with a different level of luminous intensity, such that the second rate is brighter than the first rate. Furthermore, upon reaching a third predetermined frequency threshold value, the controller 46 may disable the blower 38. However, the blower 38 may be disabled at any suitable threshold value, which may include the second predetermined frequency threshold value.

Figure 6:
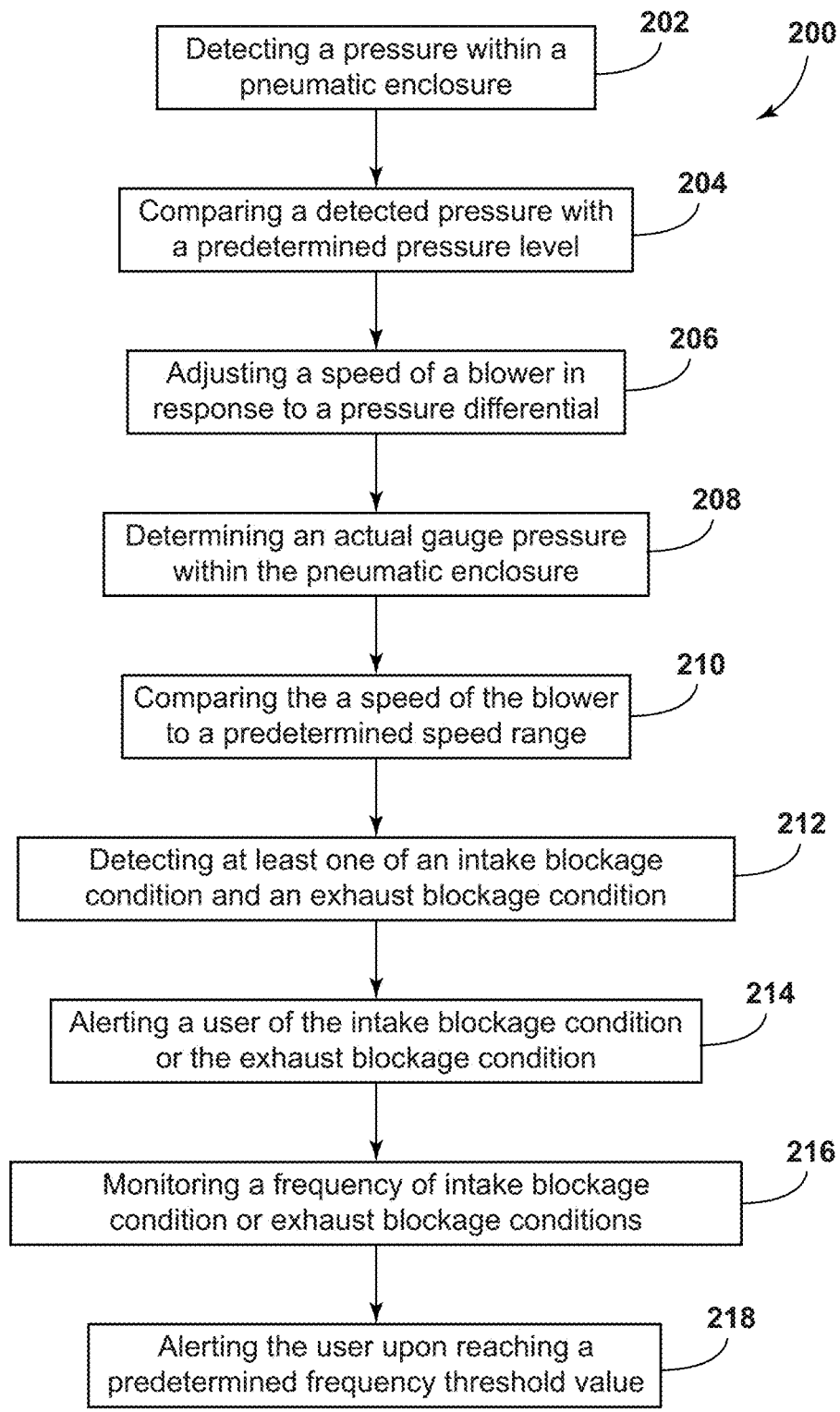
FIG. 6 is a flow diagram of a method of operating a pneumatic system according to various aspects described herein.

Referring to FIG. 6, and with further reference to FIGS. 1-5, a method 200 of operating the pneumatic system 14 includes step 202 of detecting the chamber pressure, Pc within the pneumatic enclosure 26. The pressure sensor 42 detects the chamber pressure, $P_C$ and communicates the detected pressure to the controller 46. In step 204, the controller 46 compares the chamber pressure, Pc to a predetermined pressure value. The controller 46 includes programs or algorithms stored in the memory and executable by the processor. One or more of the programs generally relate to storing the predetermined pressure value and comparing the detected chamber pressure, $P_C$ with the predetermined pressure value.

In step 206, the controller 46 is configured to adjust the speed of the blower 38 based on the comparison of the chamber pressure, $P_C$ to the predetermined pressure value (e.g., a pressure differential). If the detected chamber pressure, $P_C$ is lower than the predetermined pressure value, the controller 46 increases the speed of the blower 38 to increase the chamber pressure, $P_C$. Alternatively, if the detected chamber pressure, $P_C$ is higher than the predetermined pressure value, the controller 46 decreases the speed of the blower 38 to increase the chamber pressure, $P_C$. Accordingly, the speed of the blower 38 is adjusted to maintain the chamber pressure, $P_c$ at or about the predetermined pressure value.

In step 208, the controller 46 is configured to determine an actual pressure gauge of the pneumatic enclosure 26. The pressure sensor 42 is configured to detect ambient pressure, $P_A$. The controller 46 may compare the chamber pressure, Pc to the ambient pressure, $P_A$ to determine the actual pressure gauge.

In step 210, the controller 46 compares the speed of the blower 38 with the predetermined speed range 150. As previously explained, the predetermined speed range 150 is defined between the predetermined upper threshold value 154 and the predetermined lower threshold value 158. When the controller 46 detects that the speed of the blower 38 falls within the predetermined speed range 150, the controller 46 may determine that the blower 38, and accordingly the pneumatic system 14, is operating in ideal conditions.

In step 212, if the controller 46 detects that the blower 38 is operating at a speed at or above the predetermined upper threshold value 154, the controller 46 detects the intake blockage condition 48. If the controller 46 detects that the blower 38 is operating at a speed at or below the predetermined lower threshold value 158, the controller 46 detects the exhaust blockage condition 50. If at least one of the intake blockage condition 48 and the exhaust blockage condition 50 are detected by the controller 46, the controller 46 is configured to alert the user in step 214. The alarm signal may be an audible or visual indication on the interface 90 or the remote device 110 that indicates one or both of the intake blockage condition 48 and the exhaust blockage condition 50 are detected.

In step 216, the controller 46 is configured to monitor the frequency of the detection of the intake blockage condition 48, the exhaust blockage condition 50, or both. The controller 46 includes one or more programs for counting the detected condition, storing the count, and monitoring the frequency. In step 218, the user is alerted when the predetermined frequency threshold value is reached or exceeded. As previously explained, a first alert, such as a light of a first rate or intensity, may be used to indicate a first predetermined frequency threshold value is reached and a second alert, such as a selectively illuminating the light source 116 at a second rate or intensity, may be used to indicate a second predetermined frequency threshold value is reached. The alerts for indicating the predetermined frequency threshold value for intake blockage conditions 48 have been reached may be the same or different than the alert for indicating the predetermined frequency threshold value of the exhaust blockage conditions 50 has been reached. Moreover, in step 218, an action, such as deactivating or temporarily disabling the blower 38, may be conducted by the controller 46 when a specific predetermined frequency threshold is reached. It will be understood that the steps of the method 200 may be performed in any order, simultaneously, and/or omitted without departing from the teachings provided herein.

Use of the present device may provide for a variety of advantages. For example, the pneumatic system 14 is configured to adjust the speed of the blower 38 in response to the chamber pressure, Pc within the pneumatic enclosure 26. Additionally, the controller 46 is configured to monitor the chamber pressure, Pc and the speed of the blower 38 to detect the intake blockage condition 48 and the exhaust blockage condition 50. Moreover, when one or both of the intake blockage condition 48 and the exhaust blockage condition 50 are detected, the user may be alerted via an alarm signal. Additionally, the controller 46 is configured to monitor the frequency of one or both of the intake blockage condition 48 and the exhaust blockage condition 50. The user may be alerted when a predetermined frequency threshold for one or both of the intake blockage condition 48 and the exhaust blockage condition 50 is reached or exceeded. Additional benefits and advantages may also be realized and/or achieved.

According to one aspect of the present disclosure, a patient support apparatus pneumatic system includes a mattress that defines an interior. A pneumatic enclosure is in fluid communication with the interior. The pneumatic enclosure includes an inlet and an outlet. A blower is in fluid communication with the interior and the pneumatic enclosure. A pressure sensor is configured to detect a pressure at the outlet. A controller is configured to monitor a speed of the blower and the pressure at the outlet for detecting at least one of an intake blockage condition and an exhaust blockage condition.

According to another aspect, a controller is configured to detect an intake blockage condition when a speed of a blower is at or above a predetermined upper threshold value and an exhaust blockage condition when the speed of the blower is at or below a predetermined lower threshold value.

According to another aspect, a microclimate management layer is disposed within an interior and is in fluid communication with an outlet.

According to another aspect, an alarm and a controller is configured to output an alarm signal from the alarm upon detection of at least one of the intake blockage condition and an exhaust blockage condition.

According to another aspect, a controller is configured to monitor a frequency of detected intake blockage conditions and exhaust blockage conditions.

According to another aspect, a controller is configured to disable a blower upon reaching a predetermined frequency threshold value.

According to another aspect, a controller is configured to monitor a frequency of detected intake blockage conditions and exhaust blockage conditions. Upon reaching a first predetermined frequency threshold value. The controller is configured to selectively illuminate a light source at a first rate.

According to another aspect, a controller is configured to selectively illuminate a light source at a second rate higher than a first rate upon reaching a second predetermined frequency threshold value.

According to another aspect of the present disclosure, a pneumatic system for a patient apparatus includes a pneumatic enclosure having an inlet and an outlet. A blower is in fluid communication with the inlet via a first flexible conduit. A microclimate management layer is in fluid communication with the outlet via a second flexible conduit. A pressure sensor is configured to detect pressure within the pneumatic enclosure. A controller is configured to adjust a speed of the blower to maintain a predetermined pressure within the pneumatic enclosure. The controller is configured to detect at least one of an intake blockage condition and an exhaust blockage condition when the speed of the blower is outside a predetermined speed range.

According to another aspect, a predetermined speed range is between a predetermined upper threshold value and a predetermined lower threshold value. A controller is configured to detect an intake blockage condition when a speed of a blower is at or above the predetermined upper threshold value and an exhaust blockage condition when the speed of the blower is at or below the predetermined lower threshold value.

According to another aspect, a controller is configured to output an alarm signal when at least one of an intake blockage condition and an exhaust blockage condition is detected.

According to another aspect, a remote device is communicatively coupled to a controller. An alarm signal is at least one of an audible alarm on the remote device and a notification pushed to a display on the remote device.

According to another aspect, a controller is configured to monitor a frequency of at least one of detected intake blockage conditions and exhaust blockage conditions.

According to another aspect, a controller is configured to selectively illuminate a light source at a first rate upon reaching a first predetermined frequency threshold value and selectively illuminate the light source at a second rate upon reaching a second predetermined frequency threshold value. The second rate is different than the first rate.

According to another aspect, a controller is configured to deactivate a blower upon reaching a predetermined frequency threshold value.

According to another aspect of the present disclosure, a method of operating a mattress pneumatic system includes detecting pressure within a pneumatic enclosure. A detected pressure is compared with a predetermined pressure value. A speed of a blower is adjusted in response to a pressure differential between the detected pressure and the predetermined pressure value. The speed of the blower is compared to a predetermined speed range. A user is alerted of at least one of an intake blockage condition and an exhaust blockage condition when the speed of the blower is outside the predetermined speed range.

According to another aspect, an intake blockage condition is detected when the speed of a blower is at or above a predetermined upper threshold value of a predetermined speed range. An exhaust blockage condition is detected when the speed of the blower is at or below a predetermined lower threshold value of the predetermined speed range.

According to another aspect, a frequency is monitored of at least one of detected intake blockage conditions and detected exhaust blockage conditions.

According to another aspect, a user is alerted upon reaching a predetermined frequency threshold value of at least one of detected intake blockage conditions and detected exhaust blockage conditions.

According to another aspect, an ambient pressure is detected. A detected pressure within a pneumatic enclosure is compared with a detected ambient pressure to determine an actual gauge pressure within the pneumatic enclosure.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

The various illustrative logical blocks, modules, controllers, and circuits described in connection with the embodiments disclosed herein may be implemented or performed with application specific integrated circuits (ASICs), field programmable gate arrays (FPGAs), general purpose processors, digital signal processors (DSPs) or other logic devices, discrete gates or transistor logic, discrete hardware components, or any combination thereof designed to perform the functions described herein. A general purpose processor may be any conventional processor, controller, microcontroller, state machine or the like. A processor may also be implemented as a combination of computing devices, e.g., a combination of a DSP and a microprocessor, a plurality of microprocessors, one or more microprocessors in conjunction with a DSP core, or any other such configuration.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A pneumatic system for a patient support apparatus, comprising:
   a pneumatic enclosure having an inlet and an outlet;
   a blower in fluid communication with the inlet via a first flexible conduit;
   a microclimate management layer in fluid communication with the outlet via a second flexible conduit;
   a pressure sensor configured to detect pressure within the pneumatic enclosure; and
   a controller configured to:
      adjust a speed of the blower to maintain a predetermined pressure within the pneumatic enclosure;
      detect at least one of an intake blockage condition and an exhaust blockage condition when the speed of the blower is outside a predetermined speed range; and
      monitor and store a count of several detected blockage conditions, wherein the several detected blockage conditions include at least one of detected intake blockage conditions and detected exhaust blockage conditions, and wherein the count is a number of occurrences where the controller determines at least one of the intake blockage condition and the exhaust blockage condition is detected.

2. The pneumatic system of claim 1, wherein the predetermined speed range is between a predetermined upper threshold value and a predetermined lower threshold value, and wherein the controller is configured to detect the intake blockage condition when the speed of the blower is at or above the predetermined upper threshold value and the exhaust blockage condition when the speed of the blower is at or below the predetermined lower threshold value.

3. The pneumatic system of claim 1, wherein the controller is configured to output an alarm signal when at least one of the intake blockage condition and the exhaust blockage condition is detected.

4. The pneumatic system of claim 3, further comprising:
   a remote device communicatively coupled to the controller, wherein the alarm signal is at least one of an audible alarm on the remote device and a notification pushed to a display on the remote device.

5. The pneumatic system of claim 1, further comprising:
   a light source, wherein the controller is configured to selectively illuminate the light source at a first rate upon reaching a first predetermined frequency threshold value and selectively illuminate the light source at a second rate upon reaching a second predetermined frequency threshold value, the second rate being different than the first rate.

6. The pneumatic system of claim 1, wherein the controller is configured to deactivate the blower upon reaching a predetermined frequency threshold value.

7. The pneumatic system of claim 1, wherein the controller is configured to monitor and store the count of both of the detected inlet blockage conditions and the detected exhaust blockage conditions.

8. The pneumatic system of claim 7, wherein the count of the detected intake blockage conditions is stored separate from the count of the detected exhaust blockage conditions.

9. The pneumatic system of claim 1, wherein the pressure sensor is configured to detect the pressure within the pneumatic enclosure at the inlet and at the outlet.

10. The pneumatic system of claim 9, wherein each intake blockage condition is detected based on a pressure drop at the inlet detected by the pressure sensor.

11. The pneumatic system of claim 10, wherein the controller is configured to increase the speed of the blower in response to the detected intake blockage conditions.

12. The pneumatic system of claim 9, wherein each exhaust blockage condition is detected based on a pressure increase at the outlet detected by the pressure sensor.

13. The pneumatic system of claim 12, wherein the controller is configured to decrease the speed of the blower in response to the detected exhaust blockage conditions.

14. The pneumatic system of claim 1, further comprising:
a light source in communication with the controller, wherein the controller is configured to:
compare the count of the at least one of the detected intake blockage conditions and the detected exhaust blockage conditions to predetermined frequency threshold values, each predetermined frequency threshold value being a number of occurrences when at least one of the intake blockage condition and the exhaust blockage condition is detected;
selectively illuminate the light source at a first rate upon reaching a first predetermined frequency threshold value;
selectively illuminate the light source at a second rate upon reaching a second predetermined frequency threshold value, the second rate being different than the first rate, and wherein the second predetermined frequency threshold value is higher than the first predetermined frequency threshold value; and
deactivate the blower upon reaching a third predetermined frequency threshold value, wherein the third predetermined frequency threshold value is higher than the second predetermined frequency threshold value.

15. The pneumatic system of claim 1, wherein the pressure sensor is configured to sense ambient pressure.

16. The pneumatic system of claim 15, wherein the controller is configured to determine an actual gauge pressure within the pneumatic enclosure by determining a difference between the detected pressure within the pneumatic enclosure with detected ambient pressure.

* * * * *